United States Patent [19]

Steinstrasser et al.

[11] 4,065,489
[45] Dec. 27, 1977

[54] BIPHENYL ESTERS AND LIQUID CRYSTALLINE MIXTURES COMPRISING THEM

[75] Inventors: Rolf Steinsträsser; Fernando Del Pino, both of Darmstadt, Germany

[73] Assignee: Merck Patent Gesellschaft mit beschrankter Haftung, Darmstadt, Germany

[21] Appl. No.: 624,400

[22] Filed: Oct. 21, 1975

[30] Foreign Application Priority Data

Oct. 22, 1974 Germany .............................. 2450088
Aug. 6, 1975 Germany .............................. 2535046

[51] Int. Cl.² ............................................ C07C 69/76
[52] U.S. Cl. ...................... 560/59; 252/299;
260/515 R; 260/520 R; 260/73; 260/102;
260/108
[58] Field of Search ........................... 260/473 R, 469

[56] References Cited

U.S. PATENT DOCUMENTS

| | | | |
|---|---|---|---|
| 3,681,445 | 8/1972 | Ruyle et al. | 260/473 R |
| 3,758,442 | 9/1973 | Shima et al. | 260/473 R |
| 3,925,238 | 12/1975 | Gavrilovic | 260/473 R |
| 3,947,375 | 5/1976 | Gray | 260/473 R |

*Primary Examiner*—Paul J. Killos
*Attorney, Agent, or Firm*—Millen & White

[57] ABSTRACT

Biphenyl esters of the formula

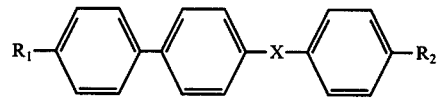

wherein X is —CO—O— or —O—CO— and $R_1$ and $R_2$ each are alkyl or alkoxy of 1 – 8 carbon atoms, enlarge significantly the temperature range of the nematic phase of liquid-crystalline compositions without adversely affecting other properties.

14 Claims, No Drawings

BIPHENYL ESTERS AND LIQUID CRYSTALLINE MIXTURES COMPRISING THEM

Background of The Invention

This invention relates to novel biphenyl esters, to liquid crystalline mixtures comprising them, and to processes for their preparation and their use as components in such mixtures, which are useful as dielectrics for liquid crystal display elements.

To an increasing extent the changes of the optical properties, such as light scattering, birefringence, reflecting power of color, of nematic or nematic-cholesteric liquid crystalline materials under the influence of an electric field are employed for converting electrical voltages pulses into optical signals. The function of such liquid crystal display elements thereby depends, for example, upon the phenomenon of dynamic scattering, the deformation of aligned phases or the Schadt-Helfrich effect in the twisted cell.

For the technical application of these effects in electronic constructional elements, liquid crystalline materials are required which satisfy a plurality of requirements. Especially important are chemical stability towards moisture, air and physical influences, such as heat, radiation in the infrared, visible and untra-violet range and electrical direct and alternating fields. Furthermore, liquid crystalline materials, to be useable, should have a liquid crystal mesophase in the temperature range of at least +10° C. to +60° C., preferably 0° C. to 60° C., and a viscosity at room temperature of not more than 70 cP. Finally, they must not exhibit any inherent absorption in the range of visible light, i.e., they must be colorless.

Colorless liquid crystalline compounds are known which satisfy the stability requirements demanded of dielectrics for electronic constructional elements, e.g., the p,p'-disubstituted benzoic acid phenyl esters described in published German Specification No. 2,139,628 (U.S. Application Ser. No. 277,502, filed 8/1/72) and the p,p'-disubstituted biphenyl derivatives described in published German Specification No. 2,356,085 (U.S. Application Ser. No. 413,247, filed 11/6/73). In both of these classes of compounds, as in the case of other known series of compounds with a liquid crystalline mesophase, there are no individual compounds which form a liquid crystalline nematic mesophase in the temperature range of 10° C. to 60° C. Therefore, as a rule, there are employed mixtures of two or more compounds which are useable as liquid crystalline dielectrics, usually a mixture of at least one compound with low melting and clear point and one having a considerably higher melting and clear point. Normally, there is obtained a mixture whose melting point lies below that of the lower melting component thereof and whose clear point lies between the clear points of the components. Optimal dielectrics cannot be prepared in this manner because the component with the high melting and clear point almost always also imparts a high viscosity to the mixture. The switch times of the electro-optical constructional elements produced therewith are thereby prolonged in an undesirable manner.

It has now been found that the biphenyl esters of this invention are exceptionally suitable as components of liquid crystalline dielectrics, imparting thereto the requisite properties without imparting thereto an undesirably high viscosity.

SUMMARY OF THE INVENTION

In a composition aspect, this invention relates to novel biphenyl esters of the general Formula I

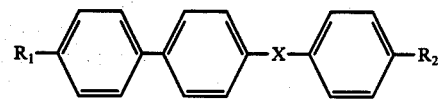

wherein X is —CO—O— or —O—CO— and $R_1$ and $R_2$, which can be alike or different, are alkyl or alkoxy of 1–8 carbon atoms in a straight or branched chain.

In other composition aspects, this invention relates to nematic mixtures of liquid crystalline compounds comprising at least one biphenyl ester of this invention which are useful as dielectrics for electronic constructional elements.

In process aspects, this invention relates to methods of making and using the compositions of this invention.

DETAILED DISCUSSION

The biphenyl derivatives of the general Formula I are biphenyl-carboxylic acid phenyl esters of the general Formula II

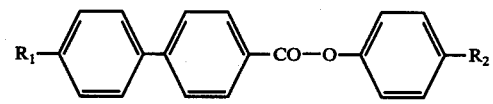

and benzoic acid biphenyl esters of the general Formula III

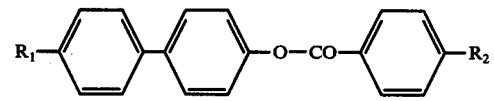

wherein $R_1$ and $R_2$ have the values given above.

These compounds exhibit a nematic and, in some cases, an additional smectic mesophase within certain temperature ranges for the same purposes as known liquid crystalline substances.

Although almost all of the compounds of the general Formula I possess such high melting (above 90° C.) and clear points (above 170° C), that they alone are unsuited as dielectrics for electronic indicator elements which are to be operated at room temperature, these compounds admixed with other liquid crystalline compounds achieve a markedly lower melting point thereof, as well as favorably improving the clear point, without, at the same time, causing an undesirably large increase in viscosity.

It has been found that those compounds of Formula I are especially well suited as components of liquid crystalline dielectrics which form both a nematic phase and a smectic phase. This is especially surprising components of liquid crystalline dielectrics which form both a nematic phase and a smectic phase. This is especially surprising because, as is known, smectic phases possess a substantially higher viscosity than nematic phases. Heretofore, no strict rules have been derived according to which, in the case of the compounds according to the invention, certain structural elements are responsible for the existence of a smectic mesophase. In the case of the compound of Formula II, smectic mesophases are observed more often than in the case of those of Formula III. For this reason, the compounds of Formula II according to the invention are preferred as components of liquid crystalline dielectrics.

In the compounds of Formula I, the $R_1$ and $R_2$ can be the same or different. Especially valuable as components of the liquid crystalline compositions of this invention are those biphenyl esters of Formula I in which at least one of $R_1$ and $R_2$ is alkyl. Especially preferred are those in which both $R_1$ and $R_2$ are alkyl of 1-8 C-atoms, e.g., methyl, ethyl, n-propyl, isopropyl, n-butyl, isobutyl, n-pentyl, 2-methyl-butyl, 3-methylbutyl, n-hexyl, 1-methyl-pentyl, n-heptyl, n-octyl and 2-ethyl hexyl. Most preferred of this latter group are those compounds of Formula I in which on of $R_1$ and $R_2$ is a straight-chain alkyl group of 1-7 carbon atoms and the other is straight-chain or branched alkyl of 3-8 carbon atoms.

Another important class of biphenyl esters of Formula I are those in which one of $R_1$ and $R_2$ is an alkyl, preferably a straight-chain alkyl group and most preferably of 3-8 carbon atoms, and the other is straight chain alkoxy, preferably of 1-6 carbon atoms, i.e., methoxy, ethoxy, n-propyloxy, n-butyloxy, n-pentyloxy or n-hexyloxy.

In a process aspect, this invention relates to the preparation of the biphenyl esters of Formula I employing reactions, such as are frequently described in the literature for the preparation of aromatic carboxylic acid esters, preferably by reacting a biphenyl compound of the general Formula IV

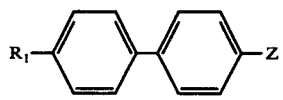

IV wherein Z is OH, OMe, wherein Me an equivalent of a metal cation, or COOH or a reactive derivative thereof, at a temperature from −50° C. to +250° C., optionally in the presence of an organic solvent and/or a conventional esterification catalyst, with a compound of the general Formula V

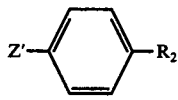

V wherein Z' is COOH or a reactive derivative thereof when Z is OH or OMe, and is OH or OMe when Z is COOH or a reactive derivative thereof. There are thus obtained compounds of the general Formula II when Z is COOH or a reactive derivative thereof, preferably —CO—halogen and especially —COCl, -COO-lower alkyl, preferably —COOCH₃, or an anhydride group, preferably a mixed anhydride, e.g., —COOCOCH₃. In a compound of Formula V,Z' is a phenolic hydroxyl group or a phenolate group, preferably an alkali metal or alkaline earth metal phenolate group. The reaction conditions for the process according to the invention are substantially determined by the nature of the Z and Z' groups. Thus, a carboxylic acid is, as a rule, reacted with a phenol (Z, Z' = COOH, OH) in the presence of a strong acid, for example, a mineral acid, such as hydrochloric acid or sulfuric acid. Preferred is the reaction of an acid anhydride or more preferably an acid chloride with a phenol (Z, Z' = COCl, OH). These esterification reactions are preferably carried out in a basic medium, employing as base, e.g., an alkali metal hydroxide, such as sodium or potassium hydroxide, an alkali metal carbonate or hydrogen carbonate, such as sodium carbonate, sodium hydrogen carbonate, potassium carbonate or potassium hydrogen carbonate, an alkali metal acetate, such as sodium or potassium acetate, an alkaline earth metal hydroxide, such as calcium hydroxide, or an organic base, such as triethylamine, pyridine, lutidine, collidine or quinoline.

The esterification is advantageously carried out in the presence of an inert solvent, e.g., an ether, such as diethyl ether, di-n-butyl ether, tetrahydrofuran, dioxane or anisole, a ketone, such as acetone, butanone, pentan-3-one or cyclohexanone, an amide, such as dimethylformamide or hexamethyl phosphoric acid triamide, a hydrocarbon, such as benzene, toluene or xylene, a halogenated hydrocarbon, such as carbon tetrachloride, or tetrachloroethylene, or a sulphoxide, such as dimethyl sulphoxide or sulfolane. Solvents which are not miscible with water can advantageously be employed simultaneously for azeotropically distilling off any water formed by the esterification. Sometimes, an excess of the organic base used, for example, pyridine, quinoline or triethylamine, can be employed as solvent for the esterification. The esterification reaction can also be carried out in the absence of a solvent, for example, by simple heating of the components in the presence of sodium acetate.

The reaction temperature usually is from −50° C. to +250° C., preferably −20° C. to +80° C. At these temperatures, the esterification reaction is usually complete after 15 minutes to 48 hours.

In a further preferred embodimental of this process aspect of the invention, the phenol to be esterified of the formula IV or V (Z or Z' = OH) is first converted into its sodium or potassium salt, for example, by treatment with ethanolic sodium or potassium hydroxide solution, the thus produced salt is isolated and, together with sodium hydrogen carbonate or potassium carbonate, is suspended, with stirring, in acetone or diethyl ether, the resulting suspension is mixed dropwise, with stirring, with a solution of an acid chloride or anhydride in diethyl ether, acetone or dimethylformamide. The reaction mixture is thereby maintained at a temperature between −25° C. and +20° C., preferably at −10° C. to −20° C. In this method, the esterification reaction is usually complete after 15 to 50 minutes.

Some of the starting materials for the process of this invention are known, such as, for example, the phenols and benzoic acids of Formula V substituted in the para-position. The others can be prepared without difficulty according to standard processes of organic chemistry from compounds known from the literature. Thus, for example, carboxylic acids of Formula IV (Z = COOH) are obtained by hydrolysis of 4-cyanobiphenyls substituted in the 4'-position, which are described in published German Specification No. 2,356,085. The alkoxy-hydroxy-biphenyls of the general Formula IV (Z = OH, $R_1$ = alkoxy) can be obtained, for example, by partial etherification of 4,4'-dihydroxybiphenyl. The alkyl-hydroxy-biphenyls of Formula IV (Z = OH, $R_1$ = alkyl) can be prepared from the 4-alkyl-4'-nitrodiphenyls described in published German Specification No. 2,356,085 by reduction to the corresponding 4'-aminodiphenyls, followed by diazotization and heating the resulting diazonium salt with water.

The compounds of Formula I can be mixed with known liquid crystalline compounds or mixture of compounds, e.g., in amounts of 0.5–40 mole percent, preferably 1 - 20 mole percent, more preferably of 5–15 mole percent.

Known liquid crystalline materials whose properties can be improved by their admixture with one or more compounds of this invention include those which have been employed as dielectrics in electrooptical indicator devices or which are suitable for this purpose, the most common of which being mixtures of derivatives of the azobenzene, azoxybenzene, biphenyl, Schiff base, especially benzylidene derivative, phenyl benzoate, optionally halogenated stilbene, diphenyl-acetylene derivative, diphenyl-nitrone and substituted cinnamic acid series. Frequently, isomer pairs and/or eutectic mixtures are employed.

The most important components of known nematic compositions are compounds of the general Formula VI:

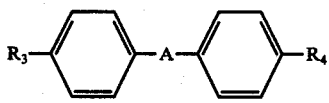

wherein A is

—CH=CH—

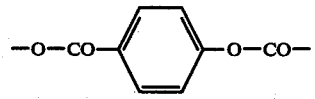

—CX'=CH—

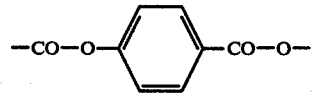

—CH=CX'—  —CH=N—
—C≡C—     —N=CH—
—N=N—     —CH=N—
                ↓
                O
—N=N—     —N=CH—
  ↓           ↓
  O           O
—N=N—     or a C—C single bond;
  ↓
  O
—O—CO—
—CO—O—

X' is halogen, preferably Cl; and $R_3$ and $R_4$ are alike or different and are cyano, nitro, or isonitrile, or alkyl, alkoxy or alkanoyloxy of up to 18, preferably up to 8 carbon atoms. In most of these compounds, $R_3$ and $R_4$ are preferably different, one usually being alkyl or alkoxy. However, all other variants are also suitable. A whole series of such nematic compositions are commercially available.

The nematic compositions can sometimes be modified by the addition thereto of cholesteric compounds, to achieve memory effects, usually in an amount of up to about 10 mole percent. A large number of nematic substances is described e.g., in published German Specifications Nos. 1,951,092; 2,014,989 (U.S. Pat. No. 3,773,747); 2,139,628; 2,201,122; and 2,356,085, whose disclosures are incorporated by reference.

By the addition of 0.5 to 40, preferably of 1 - 20, mole percent of one or more compounds of Formula I to a known liquid crystalline compound or mixture of compounds with a melting point in the range of room temperature or below and clear points of 50° C. or above, the range of the liquid crystalline mesophase is, surprisingly, widened. Frequently, this widening takes place at both ends, i.e., the melting point, even of low melting mixtures, is further lowered and the clear point is further raised. In this way, many liquid crystalline compositions which, because of an unfavorable position or limited breadth of the temperature range of their nematic mesophase, were not suitable for use as dielectrics, are now suitable for this purpose. The influence of the compounds of this invention on the viscosity of the dielectrics is especially favorable for this purpose. Heretofore, the viscosity was frequently increased too much by the addition of a compound with a high clear point, for example, of the p-benzoyloxybenzoic acid phenyl ester series, so that mixtures of this type in displays exhibited switch times which were too long to be technically useable to a great extent. Surprisingly, such a large increase in viscosity does not occur by the addition of the biphenyl esters of this invention.

The liquid crystalline compositions of this invention are suitable for use as dielectrics in electrooptical displays used at room temperature, have a liquid crystal mesophase from at least 10° to 60°, preferably at least 0° to 60° C., and comprise A. 99.5–60, preferably 99–80, more preferably 95–85, mole percent of at least one compound, e.g., one or a mixture of two, three, four, five or more compounds having a nematic phase, or forming such phase in admixture with one another, at least one preferably being a compound of Formula VI, having, in the absence of a compound of Formula I, a liquid crystal mesophase beginning above about 45°, preferably about 20° C, and ending in the range of about 40° C, preferably about 55° C., and B. 0.5–40, preferably 1–20, more preferably 95–85, mole percent of at least one compound, e.g., one or a mixture of two, three or more compounds, of Formula I.

Liquid crystalline mixtures according to the invention containing at least one compound of the general Formula I can be employed as dielectrics in all types of liquid crystal displays which have hitherto been known. By means of the additions of the new biphenyl esters, the values of the dielectric anisotropy of the liquid crystalline basis substances are only insubstantially changed. Therefore, by a suitable choice of the basis substances, it is possible to prepare dielectrics according to the invention with positive and negative dielectric anisotropy. Furthermore, the dielectrics according to the invention can contain additives which influence the conductivity, the ability of orientation and/or the sign and value of the dielectric anisotropy additives of this kind are described, for example, in published German Specifications Nos. 2,209,127, 2,240,864 and 2,321,632.

Without further elaboration, it is believed that one skilled in the art can, using the preceding description, utilize the present invention to its fullest extent. The following Preferred specific embodiments are, therefore, to be construed as merely illustrative, and not limitative of the remainder of the disclosure in any way whatsoever.

In the Examples, m.p. means melting point, S/N is the temperature of the phase transition from a smectic into a nematic phase and K. is the clear point of a substance. Unless stated otherwise, percentages of the reactants and/or solvents are by weight.

EXAMPLE 1 a. 5 g. 4-cyano-4'-n-pentylbiphenyl in a mixture of 90 ml. ethylene glycol, 18 ml. water and 3.2 g. sodium hydroxide are heated while stirring to 125° C. for 8 hours. After cooling, the reaction mixture is filtered, the residue suspended in 50 ml. ethanol and acidified with 5% hydrochloric acid to a pH of about 2. The reaction mixture is further stirred for 4 hours at room temperature, then filtered and the residue washed with ethanol. The 4-(4-n-pentylphenyl)-benzoic acid obtained is recrystallized from chloroform; m.p. 174° C., S/N 200° C., K. 254° C.

There are prepared analogously:

4-(4-ethylphenyl)-benzoic acid,
4-(4-n-propylphenyl)-benzoic acid,
4-(4-n-butylphenyl)-benzoic acid,
4-(4-n-hexylphenyl)-benzoic acid,
4-(4-n-heptylphenyl)-benzoic acid, m.p. 148° C., S/N 230° C., K.247° C.,
4-(4-n-octylphenyl)-benzoic acid,
4-(4-methoxyphenyl)-benzoic acid, m.p. 258° C., K. 300° C.,
4-(4-ethoxyphenyl)-benzoic acid, m.p. 256° C., K. 302° C.,
4-(4-n-propyloxyphenyl)-benzoic acid, m.p. 249° C., K. 275° C.,
4-(4-n-butyloxyphenyl)-benzoic acid, m.p. 234° C., K. 285° C., 4-(4-n-pentyloxyphenyl)-benzoic acid, m.p. 224° C., K. 270° C.,
4-(4-n-hexyloxyphenyl)-benzoic acid, m.p. 213° C., S/N 243° C., K. 274° C., 4-(4-n-heptyloxyphenyl)-benzoic acid, m.p. 198° C., S/N 238° C., K. 240° C.,
4-(4-n-octyloxyphenyl)-benzoic acid, m.p. 204° C., S/N 233° C., K. 235° C.

b. 14 g. 4-(4-n-pentylphenyl)-benzoic acid and 9 g. 4-n-pentylphenol are heated with 0.25 g. concentrated sulfuric acid and 0.15 g. boric acid in 250 ml. toluene to the boil, under reflux, for 24 hours in a round-bottomed flask equipped with a water separator. About 0.8 ml. water is separated azeotropically. The reaction mixture is washed three times with 200 ml. portions of water, once with 200 ml. 5% aqueous sodium bicarbonate solution and then twice again with 200 ml. portions of water and then dried over sodium sulfate. After distilling off the toluene, the 4-(4-n-pentylphenyl)-benzoic acid 4'-n-pentylphenyl ester obtained is recrystallized from methanol; m.p. 93° C.; S/N 145° C; K. 175° C.

There are prepared analogously:

4-(p-toluyl)-benzoic acid 4'-methylphenyl ester,
4-(p-toluyl)-benzoic acid 4'-ethylphenyl ester,
4-(p-toluyl)-benzoic acid 4'-hexylphenyl ester, 4-(4-ethylphenyl)-benzoic acid 4'-ethylphenyl ester,
4-(4-ethylphenyl)-benzoic acid 4'-n-butylphenyl ester,
4-(4-ethylphenyl)-benzoic acid 4'-n-pentylphenyl ester,
4-(4-ethylphenyl)-benzoic acid 4'-n-octylphenyl ester,
4-(4-n-propylphenyl)-benzoic acid 4'-methylphenyl ester,
4-(4-n-propylphenyl)-benzoic acid 4'-n-propylphenyl ester,
4-(4-n-propylphenyl)-benzoic acid 4'-n-hexylphenyl ester,
4-(4-n-butylphenyl)benzoic acid 4'-methylphenyl ester,
4-(4-n-butylphenyl)-benzoic acid 4'-n-butylphenyl ester,
4-(n-n-butylphenyl)-benzoic acid 4'-n-pentylphenyl ester, m.p. 97.5° C., S/N 138° C., K. 169° C.;
4-(4-n-butylphenyl)-benzoic acid 4'-n-heptylphenyl ester,
4-(4-n-butylphenyl)-benzoic acid 4'-n-octylphenyl ester,
4-(4-n-pentylphenyl)-benzoic acid 4'-ethylphenyl ester, m.p. 106° C., S/N 144° C., K. 174° C.;
4-(4-n-pentylphenyl)-benzoic acid 4'-n-propylphenyl ester, m.p. 108° C., S/N 142° C., K. 178° C.;
4-(4-n-pentylphenyl)-benzoic acid 4'-n-butylphenyl ester, m.p. 104° C., S/N 144° C., K. 174° C.,
4-(4-n-pentylphenyl)-benzoic acid 4'-n-hexylphenyl ester, m.p. 93° C., S/N 145° C., K. 163° C.;
4-(4-n-pentylphenyl)-benzoic acid 4'-n-heptylphenyl ester, 4-(4-n-pentylphenyl)-benzoic acid 4'-n-octylphenyl ester,
4-(4-n-hexylphenyl)-benzoic acid 4'-ethylphenyl ester,
4-(4-n-hexylphenyl)-benzoic acid 4'-butylphenyl ester, m.p. 101° C., S/N 148° C., K. 163° C.;
4-(4-n-hexylphenyl)-benzoic acid 4'-n-pentylphenyl ester, m.p. 94.5° C., S/N. 155° C., K. 169° C.;
4-(4-n-hexylphenyl)-benzoic acid 4'-n-heptylphenyl ester,
4-(4-n-hexylphenyl)-benzoic acid 4'-n-hexylphenyl ester,
4-(4-n-heptylphenyl)-benzoic acid 4'-methylphenyl ester,
4-(4-n-heptylphenyl)-benzoic acid 4'-ethylphenyl ester, m.p. 107° C., S/N 147° C., K. 165° C.,
4-(4-n-heptylphenyl)-benzoic acid 4'-n-propylphenyl ester, m.p. 97° C., S/N 155.5° C., K. 174° C.; 4-(4-n-heptylphenyl)-benzoic acid 4'-n-butylphenyl ester, m.p. 96° C., S/N 156° C., K. 166° C.;
4-(4-heptylphenyl)-benzoic acid 4'-n-pentylphenyl ester, m.p. 98° C., S/N 159° C., K. 168° C.;
4-(4-n-heptylphenyl)-benzoic acid 4'-n-hexylphenyl ester, m.p. 97.5° C., S/N 158.5° C., K. 161.5° .;
4-(4-n-heptylphenyl)-benzoic acid 4'-n-heptylphenyl ester,
4-(4-n-heptylphenyl)-benzoic acid 4°-n-octylphenyl ester,
4-(4-n-octylphenyl)-benzoic acid 4'-methylphenyl ester,
4-(4-n-Octylphenyl)-benzoic acid 4'-n-propylphenyl ester,
4-(4-n-octylphenyl)-benzoic acid 4'-n-butylphenyl ester,
4-(4-n-octylphenyl)-benzoic acid 4'-n-pentylphenyl ester,
4-(4-n-propylphenyl)-benzoic acid 4'-(3-methylbutyl)-phenyl ester, m.p. 111.5° C., S/N 141° C., K. 163° C;
4-(4-isopropylphenyl)-benzoic acid 4'-n-pentylphenyl ester, m.p. 73° C., K. 135° C.;
4-(4-isopropylphenyl)-benzoic acid 4'-n-heptylphenyl ester, m.p. 69° C., K. 120° C.;
4-[4-(2-methylbutyl)-phenyl]-benzoic acid 4'-n-pentylphenyl ester, m.p. 65° C., K. 142° C.,
4-[4-(3-methylbutyl)-phenyl]-benzoic acid 4'-n-pentylphenyl ester, m.p. 113° C., S/N 129° C., K. 153° C.;
4-[4-(1-methylpentyl)-phenyl]-benzoic acid 4'-n-pentylphenyl ester, m.p. 50.5° C., K. 64.6° C.;

4-[4-(2-ethylhexyl)-phenyl]]-benzoic acid 4'-pentylphenyl ester, m.p. 68° C., K. 75.5° C.

EXAMPLE 2

To a boiling solution of 16.5 g. 4-methoxyphenol and 10 ml. pyridine in 120 ml. toluene, there is added dropwise, while stirring, over a period of 2 hours, a solution of 33.8 g. 4-(4-n-pentylphenyl)-benzoyl chloride [prepared by the reaction of 4-(4-n-pentylphenyl)-benzoic acid, obtained according to Example 1 (a), with thionyl chloride] in 120 ml. toluene. The reaction mixture is heated to the boil under reflux for a further 3 hours and then evaporated. The residue is mixed with 100 ml. water and extracted three times with 150 ml. portions of diethyl ether. The ether extracts are washed with 200 ml. water, 150 ml. 5% sodium hydrogen carbonate solution and again with 200 ml. water and dried over sodium sulfate. After distilling off the ether, the remaining 4-(4-n-pentylphenyl)-benzoic acid 4'-methoxyphenyl ester is recrystallized from ethanol; m.p. 100° C., S/N 120° C., K. 219° C.

There are prepared analogously:

4-(p-toluyl)-benzoic acid 4'-n-butyloxyphenyl ester,
4-(p-toluyl)-benzoic acid 4'-n-pentyloxyphenyl ester,
4-(p-toluyl)-benzoic acid 4'-n-hexyloxyphenyl ester,
4-(p-toluyl)-benzoic acid 4'-n-heptyloxyphenyl ester,
4-(4-ethylphenyl)-benzoic acid 4'-methoxyphenyl ester,
4-(4-ethylphenyl)-benzoic acid 4'-ethoxyphenyl ester,
4-(4-ethylphenyl)-benzoic acid 4'-n-hexyloxyphenyl ester,
4-(4-ethylphenyl)-benzoic acid 4'-n-octyloxphenyl ester,
4-(4-n-propylphenyl)-benzoic acid 4'-n-propyloxyphenyl ester,
4-(4-n-propylphenyl)-benzoic acid 4'-n-butyloxyphenyl ester,
4-(4-n-propylphenyl)-benzoic acid 4'-n-pentyloxyphenyl ester,
4-(4-n-propylphenyl)-benzoic acid 4'-n-heptyloxyphenyl ester,
4-(4-n-butylphenyl)-benzoic acid 4'-methoxyphenyl ester, m.p. 115° C., K. 213° C.;
4-(4-n-butylphenyl)-benzoic acid 4'-n-butyloxyphenyl ester,
4-(4-n-butylphenyl)-benzoic acid 4'-n-hexyloxyphenyl ester,
4-(4-n-butylphenyl)-benzoic acid 4'-n-octyloxyphenyl ester,
4-(4-n-pentylphenyl)-benzoic acid 4'-ethoxyphenyl ester, m.p. 122° C., S/N 132° C., K. 218° C.;
4-(4-n-pentylphenyl)-benzoic acid 4'-n-propyloxyphenyl ester, m.p. 129.5° C., S/N 151° C., K. 203° C.;
4-(4-n-pentylphenyl)-benzoic acid 4'-n-butyloxyphenyl ester, m.p. 116° C., S/N 154° C., K. 205° C.;
4-(4-n-pentylphenyl)-benzoic acid 4'-n-pentyloxyphenyl ester,
4-(4-n-pentylphenyl)-benzoic acid 4'-n-hexyloxyphenyl ester, m.p. 108° C., S/N 160° C., K. 190° C.;
4-(4-n-pentylphenyl)-benzoic acid 4'-n-heptyloxyphenyl ester,
4-(4-n-pentylphenyl)-benzoic acid 4'-n-octyloxyphenyl ester,
4-(4-n-hexylphenyl)-benzoic acid 4'-methoxyphenyl ester,
4-(4-n-hexylphenyl)-benzoic acid 4'-n-propyloxyphenyl ester, m.p. 123° C., S/N 160° C., K. 195° C.;
4-(4-n-hexylphenyl)-benzoic acid 4'-pentyloxyphenyl ester, m.p 104.5° C., S/N 169° C., K. 188° C.;
4-(4-n-hexylphenyl)-benzoic acid 4'-hexyloxyphenyl ester,
4-(4-n-hexylphenyl)-benzoic acid 4'-n-octyloxyphenyl ester,
4-(4-n-heptylphenyl)-benzoic acid 4'-methoxyphenyl ester, m.p. 104° C., S/N 137° C., K. 196° C.;
4-(4-n-heptylphenyl)-benzoic acid 4'-ethoxyphenyl ester, m.p. 107° C., S/N 157° C., K. 203° C.;
4-(4-n-heptylphenyl)-benzoic acid 4'-n-propyloxyphenyl ester, m.p. 108° C., S/N 164° C., K. 190° C.;
4-(4-n-heptylphenyl)-benzoic acid 4'-butyloxyphenyl ester, m.p. 106° C., S/N 170° C., K. 190° C.;
4-(4-n-heptylphenyl)-benzoic acid 4'-n-pentyloxyphenyl ester, m.p. 106° C., S/N 170° c., K. 183° C.;
4-(4-n-heptylphenyl)-benzoic acid 4'-hexyloxyphenyl ester, m.p. 106° C., S/N 172° C., K. 184° C.;
4-(4-n-heptylphenyl)-benzoic acid 4'-n-heptyloxyphenyl ester,
4-(4-n-heptylphenyl)-benzoic acid 4'-n-octyloxyphenyl ester,
4-(4-n-octylphenyl)-benzoic acid 4'-ethoxyphenyl ester,
4-(4-n-octylphenyl)-benzoic acid 4'-n-butyloxyphenyl ester,
4-(4-octylphenyl)-benzoic acid 4'-n-pentyloxyphenyl ester,
4-(4-n-octylphenyl)-benzoic acid 4'-n-heptyloxyphenyl ester,

EXAMPLE 3

12.6 g. potassium 4-n-butylphenolate and 5.6 g. sodium hydrogen carbonate are suspended at −10° C. in 400 ml. diethyl ether. A solution of 20.5 g. 4-(4-n-propyloxyphenyl)-benzoyl chloride [prepared by the reaction of 4-(4-n-propyloxyphenyl)-benzoic acid with thionyl chloride] in 250 ml. diethyl ether is added dropwise thereto, with stirring and cooling, at such a rate that the temperature does not rise above −10° C. The reaction mixture is thereafter warmed to +20° C. and stirred at this temperature for a further 30 minutes. The mixture is then filtered, the filtrate dried over sodium sulfate and evaporated. The remaining 4-(4-n-propyloxyphenyl)-benzoic acid 4'-n-butylphenyl ester is recrystallized from ethanol.

There are prepared analogously:

4-(4-methoxyphenyl)-benzoic acid 4'-n-butylphenyl ester,
4-(4-methoxyphenyl)-benzoic acid 4'-n-pentylphenyl ester,
4-(4-methoxyphenyl)-benzoic acid 4'-n-hexylphenyl ester,
4-(4-methoxyphenyl)-benzoic acid 4'-n-heptylphenyl ester,
4-(4-methoxyphenyl)-benzoic acid 4'-octylphenyl ester,
4-(4-ethoxyphenyl)-benzoic acid 4'-ethylphenyl ester,
4-(4-ethoxyphenyl)-benzoic acid 4'-n-pentylphenyl ester,
4-(4-ethoxyphenyl)-benzoic acid 4'-n-hexylphenyl ester,
4-(4-ethoxyphenyl)-benzoic acid 4'-n-octylphenyl ester,
4-(4-propyloxyphenyl)-benzoic acid 4-methylphenyl ester,
4-(4-n-propyloxyphenyl)-benzoic acid 4'-n-propylphenyl ester,
4-(4-n-propyloxyphenyl)-benzoic acid 4-n-pentylphenyl ester,
4-(4-n-butyloxyphenyl)-benzoic acid 4'-methylphenyl ester, 4-(4-n-butyloxyphenyl)-benzoic acid 4'-ethylphenyl ester,
4-(4-n-butyloxyphenyl)-benzoic acid 4'-n-butylphenyl ester,
4-(4-n-butyloxyphenyl)-benzoic acid 4'-n-hexylphenyl ester,
4-(4-n-butyloxyphenyl)-benzoic acid 4'-n-octylphenyl ester,
4-(4-n-pentyloxyphenyl)-benzoic acid 4'-methylphenyl ester,
4-(4-n-pentyloxyphenyl)-benzoic acid 4'-ethylphenyl ester,
4-(4-n-pentyloxyphenyl)-benzoic acid 4'-n-propylphenyl ester,
4-(4-n-pentyloxyphenyl)-benzoic acid 4'-n-butylphenyl ester,
4-(4-n-pentyloxyphenyl)-benzoic acid 4'-n-pentylphenyl ester,
4-(4-n-pentyloxyphenyl)-benzoic acid 4'-n-hexylphenyl ester,
4-(4-n-pentyloxyphenyl)-benzoic acid 4'-n-heptylphenyl ester,
4-(4-n-pentyloxyphenyl)-benzoic acid 4'-n-octylphenyl ester,
4-(4-n-hexyloxyphenyl)-benzoic acid 4'-n-methylphenyl ester,
4-(4-n-hexyloxyphenyl)-benzoic acid 4'-n-butylphenyl ester,
4-(4-n-hexyloxyphenyl)-benzoic acid 4'-n-pentylphenyl ester,
4-(4-n-hexyloxyphenyl)-benzoic acid 4'-n-hexylphenyl ester,
4-(4-n-heptyloxyphenyl)-benzoic acid 4'-methylphenyl ester,
4-(4-n-heptyloxyphenyl)-benzoic acid 4'-ethylphenyl ester,
4-(4-n-heptyloxyphenyl)-benzoic acid 4'-n-butylphenyl ester,
4-(4-n-heptyloxyphenyl)-benzoic acid 4'-n-pentylphenyl ester,
4-(4-n-heptyloxyphenyl)-benzoic acid 4'-n-hexylphenyl ester,
4-(4-n-octyloxyphenyl)-benzoic acid 4'-methylphenyl ester,
4-(4-n-octyloxyphenyl)-benzoic acid 4'-ethylphenyl ester,
4-(4-n-octyloxyphenyl)-benzoic acid 4'-n-propylphenyl ester,
4-(4-n-octyloxyphenyl)-benzoic acid 4'-n-butylphenyl ester,
4-(4-n-octyloxyphenyl)-benzoic acid 4'-n-pentylphenyl ester,
4-(4-n-octyloxyphenyl)-benzoic acid 4'-n-hexylphenyl ester,
4-(4-n-octyloxyphenyl)-benzoic acid 4'-n-octylphenyl ester.

EXAMPLE 4

To a boiling solution of 2.4 g. 4-(4-n-pentylphenyl)-phenol and 0.8 g. pyridine in 10 ml. water-free benzene is added dropwise a mixture of 1.7 g. anisoyl chloride and 2 ml. benzene in 15 minutes. The reaction mixture is further heated for 2½ hours while stirring. After cooling, the reaction mixture is filtered, the filtrate is washed with 10 ml. portions of water, 5% sodium hydrogen carbonate solution and water and dried over sodium sulfate. After distilling off the benzene, the remaining 4-methoxybenzoic acid 4'-(4-n-pentylphenyl)-phenyl ester is recrystallized from a mixture of 35 ml. ethanol and 10 ml. acetic acid ethyl ester; m.p. 114.5° C., K. 214° C.

There are obtained analogously:

4-methoxybenzoic acid 4'-(4-n-propylphenyl)-phenyl ester, m.p. 143° C., K. 231° C.;
4-methoxybenzoic acid 4'-(4-n-butylphenyl)-phenyl ester, m.p. 116° C., K. 215° C.;
4-methoxybenzoic acid 4'-(4-n-hexylphenyl)-phenyl ester,
4-methoxybenzoic acid 4'-(4'-n-heptylphenyl)-phenyl ester,
4-methoxybenzoic acid 4'-(4-n-octylphenyl)-phenyl ester,
4-ethoxybenzoic acid 4'-(4-n-butylphenyl)-phenyl ester,
4-ethoxybenzoic acid 4'-(4-n-pentylphenyl)-phenyl ester, m.p. 116° C., K. 212° C.;
4-ethoxybenzoic acid 4'-(4-n-hexylphenyl)-phenyl ester,
4-ethoxybenzoic acid 4'-(4-n-octylphenyl)-phenyl ester,
4-n-propyloxybenzoic acid 4'-(4-methylphenyl)-phenyl ester,
4-n-propyloxybenzoic acid 4'-(4-n-propylphenyl)-phenyl ester,
4-n-propyloxybenzoic acid 4'-(4-n-pentylphenyl)-phenyl ester,
4-n-propyloxybenzoic acid 4'-(4-n-octylphenyl)-phenyl ester,
4-n-butyloxybenzoic acid 4'-(4-ethylphenyl)-phenyl ester,
4-n-butyloxybenzoic acid 4'-(4-n-butylphenyl)-phenyl ester,
4-n-butyloxybenzoic acid 4'-(4-n-pentylphenyl)-phenyl ester, m.p. 109° C., K. 218° C.;
4-n-butyloxybenzoic acid 4'-(4-n-heptylphenyl)-phenyl ester,
4-n-pentyloxybenzoic acid 4'-(4-methylphenyl)-phenyl ester,
4-n-pentyloxybenzoic acid 4'-(4-n-butylphenyl)-phenyl ester,
4-n-pentyloxybenzoic acid 4'-(4-n-pentylphenyl)-phenyl ester, 4-n-pentyloxybenzoic acid 4'-(4-n-hexylphenyl)-phenyl ester,
4-n-hexyloxybenzoic acid 4'-(4-methylphenyl)-phenyl ester,
4-n-hexyloxybenzoic acid 4'-(4-ethylphenyl)-phenyl ester,
4-n-hexyloxybenzoic acid 4'-(4-n-propylphenyl)-phenyl ester,
4-n-hexyloxybenzoic acid 4'-(4-n-butylphenyl)-phenyl ester,
4-n-hexyloxybenzoic acid 4'-(4-n-pentylphenyl)-phenyl ester, m.p. 109° C., K. 190° C.;
4-n-hexyloxybenzoic acid 4'-(4-n-hexylphenyl)-phenyl ester,
4-n-hexyloxybenzoic acid 4'-(4-n-heptylphenyl)-phenyl ester, 4-n-hexyloxybenzoic acid 4'-(4-n-octylphenyl)-phenyl ester,
4-n-heptyloxybenzoic acid 4'-(4-methylphenyl)-phenyl ester,
4-n-heptyloxybenzoic acid 4'-(4-n-butylphenyl)-phenyl ester,
4-n-heptyloxybenzoic acid 4'-(4-n-pentylphenyl)-phenyl ester,
4-n-heptyloxybenzoic acid 4'-(4-n-heptylphenyl)-phenyl ester, 4-n-octyloxybenzoic acid 4'-(4-ethylphenyl)-phenyl ester,
4-n-octyloxybenzoic acid 4'-(4-n-propylphenyl)-phenyl ester,
4-n-octyloxybenzoic acid 4'-(4-n-hexylphenyl)-phenyl ester,
4-n-octyloxybenzoic acid 4'-(4-n-octylphenyl)-phenyl ester.

EXAMPLE 5

To a solution of 11 g. 4-(4-n-propylphenyl)-phenol and 10 ml. pyridine in 100 ml. toluene is added dropwise at 100° C., while stirring, over a period of 30 minutes, a solution of 10 g. 4-butylbenzoyl chloride in 40 ml. toluene. The reaction mixture is subsequently heated to the boil for 2 hours, cooled and then filtered. The filtrate is successively washed with 75 ml. amounts of water, 5% aqueous sodium hydrogen carbonate solution and water, dried over sodium sulfate and evaporated. The remaining 4-butylbenzoic acid 4'-(4-n-propylphenyl)-phenyl ester is recrystallized from ethanol; m.p. 94° C., K. 181° C.

There is obtained analogously:

4-methylbenzoic acid 4'-(4-n-pentylphenyl)-phenyl ester, m.p. 106° C., K. 180° C.;
4-ethylbenzoic acid 4'-(4-n-butylphenyl)-phenyl ester,
4-ethylbenzoic acid 4'-(4-n-pentylphenyl)-phenyl ester,
4-ethylbenzoic acid 4'-(4-n-hexyphenyl)-phenyl ester,
4-ethylbenzoic acid 4'-(4-n-octylphenyl)-phenyl ester,
4-n-propylbenzoic acid 4'-(4-n-propylphenyl)-phenyl ester,
4-n-propylbenzoic acid 4'-(4-n-butylphenyl)-phenyl ester,
4-n-propylbenzoic acid 4'-(4-n-pentylphenyl)-phenyl ester, 4-n-propylbenzoic acid 4'-(4-n-hexylphenyl)-phenyl ester,
4-n-butylbenzoic acid 4'-(4-methylphenyl)-phenyl ester,
4-n-butylbenzoic acid 4'-(4-ethylphenyl)-phenyl ester,
4-n-butylbenzoic acid 4'-(4-n-butylphenyl)-phenyl ester, m.p. 95° C., K. 168° C.;
4-n-butylbenzoic acid 4'-(4-n-pentylphenyl)-phenyl ester, m.p. 97° C., K. 170° C.;
4-n-butylbenzoic acid 4'-(4-n-hexylphenyl)-phenyl ester, m.p. 78° C., K. 159° C.;
4-n-butylbenzoic acid 4'-(4-n-heptylphenyl)-phenyl ester,
4-n-butylbenzoic acid 4'-(4-n-octylphenyl)-phenyl ester,
4-n-pentylbenzoic acid 4'-(4-methylphenyl)-phenyl ester,
4-n-pentylbenzoic acid 4'-(4-ethylphenyl)-phenyl ester,
4-n-pentylbenzoic acid 4'-(4-n-propylphenyl)-phenyl ester,
4-n-pentylbenzoic acid 4'-(4-isopropylphenyl)-phenyl ester, m.p. 95° C., K. 164° C.;
4-n-pentylbenzoic acid 4'-(4-n-butylphenyl)-phenyl ester,
4-n-pentylbenzoic acid 4'-(4-n-pentylphenyl)-phenyl ester,
4-n-pentylbenzoic acid 4'-(4-n-hexylphenyl)-phenyl ester, m.p. 90° C., S/N 97° C., K. 163° C.;
4-n-pentylbenzoic acid 4''-(4-n-heptylphenyl)-phenyl ester,
4-n-hexylbenzoic acid 4'-(4-methylphenyl)-phenyl ester,
4-n-hexylbenzoic acid 4'-(4-ethylphenyl)-phenyl ester,
4-n-hexylbenzoic acid 4'-(4-n-propylphenyl)-phenyl ester,
4-n-hexylbenzoic acid 4'-(4-n-butylphenyl)-phenyl ester,
4-n-hexylbenzoic acid 4'-(4-n-pentylphenyl)-phenyl ester, m.p. 99° C., K. 164° C.;
4-n-hexylbenzoic acid 4'-(4-n-hexylphenyl)-phenyl ester,
4-n-hexylbenzoic acid 4'(4-n-heptylphenyl)-phenyl ester,
4-n-hexylbenzoic acid 4'-(4-n-octylphenyl)-phenyl ester,
4-n-heptylbenzoic acid 4'-(4-methylphenyl)-phenyl ester,
4-n-heptylbenzoic acid 4'-(4-ethylphenyl)-phenyl ester,
4-n-heptylbenzoic acid 4'-(4-isopropylphenyl)-phenyl ester, m.p. 82.5° C., K. 152.5° C.;
4-n-heptylbenzoic acid 4'-(4-n-butyhlphenyl)-phenyl ester, 4-n-heptylbenzoic acid 4'-(4-n-hexylphenyl)-phenyl ester,
4-n-octylbenzoic acid 4'-(4-methylphenyl)-phenyl ester,
4-n-octylbenzoic acid 4'-(4-ethylphenyl)-phenyl ester,
4-n-octylbenzoic acid 4'-(4-n-propylphenyl)-phenyl ester,
4-n-octylbenzoic acid 4'-(4-n-pentylphenyl)-phenyl ester,
4-n-octylbenzoic acid 4'-(4-n-octylphenyl)-phenyl ester, In the following Examples of liquid crystal compositions useful as dielectrics, percentages are mole percent.

EXAMPLE 6

15.7% N-(4-methoxybenzylidene)-p-butylaniline
34.9% N-(4-ethoxybenzylidene)-p-butylaniline
27.0% anisic acid 4-n-pentylphenyl ester
11.0% 4-n-hexyloxybenzoic acid 4'-n-pentylphenyl ester 3.9% 4-(4-n-hexyloxybenzoyloxy)-benzoic acid (4'-n-butyl-2'-cyanophenyl) ester
7.5% 4-(n-pentylphenyl)-benzoic acid 4'-n-pentylphenyl ester m.p. < −10° C., K. 69° C.

EXAMPLE 7

37.2% 4-cyano-4'-n-pentylbiphenyl
21.0% 4-cyano-4'-n-heptylbiphenyl
11.4% 4-cyano-4'-n-pentyloybiphenyl
11.4% 4-cyano-4'-n-heptyloxybiphenyl
13.4% 4-cyano-4'-n-octyloxybiphenyl
5.6% 4-(n-pentylphenyl)-benzoic acid 4'-n-butylphenyl ester m.p. −6° C., K. 60° C.

EXAMPLE 8

51.9% 4-cyano-4'-n-pentylbiphenyl
24.6% 4-cyano-4'-n-heptylbiphenyl
17.9% 4-cyano-4'-n-octylbiphenyl
5.6% 4-n-hexloxybenzoic acid 4'-(4-n-pentylphenyl)-phenyl ester m.p. 2° C., K. 61° C.

EXAMPLE 9

31.3% 4-cyano-4'-n-pentylbiphenyl
18.0% 4-cyano-4'-n-heptylbiphenyl
9.5% 4-cyano-4'-n-propyloxybiphenyl
10.4% 4-cyano-4'-n-pentyloxybiphenyl
10.4% 4-cyano-4'-n-heptyloxybiphenyl 15.2% 4-cyano-4'-n-octyloxybiphenyl
5.2-4-n-hexylbenzoic acid 4'-(4-n-pentylphenyl)-phenyl ester m.p. 3° C., K. 66° C.

EXAMPLE 10

37.2% 4-cyano-4'-n-pentylbiphenyl
24.1% 4-cyano-4'-n-heptylbiphenyl
14.0% 4-cyano-4'-n-pentyloxybiphenyl
17.6% 4-cyano-4'-octyloxybiphenyl
7.1% 4-(4-n-pentylophenyl)-benzoic acid 4'-n-propylphenyl ester m.p. 2° C., K. 59° C.

EXAMPLE 11

36.0% 4-cycano-4'-n-pentylbiphenyl
23.4% 4-cyano-4'-n-heptylbiphenyl
13.4% 4-cyano-4'-n-pentyloxybiphenyl
17.2% 4-cyano-4'-n-octyloxybiphenyl
4.7% 4-(4-n-pentylphenyl)-benzoic acid 4'-n-pentylpenyl ester
5.3% 4-(4-n-pentylphenyl)-benzoic acid 4'-methoxyphenyl ester m.p. 0° C., K. 66° C.

EXAMPLE 12

51.7% 4-cyano-4'-n-pentylbiphenyl
27.8% 4-cyano-4'-n-heptylbiphenyl
16.3% 4-cyano-4'-n-octyloxybiphenyl
4.2% 4-(4-n-pentylphenyl)-benzoic acid 4'-pentylphenyl ester m.p. < −10° C., K. 54° C.

EXAMPLE 13

49.3% 4-cyano-4'-n-pentylbiphenyl
26.5% 4-cyano-4'-n-heptylbiphenyl
15.5% 4-cyano-4'-n-octyloxybiphenyl
8.7% 4-(4-n-pentylphenyl)-benzoic acid 4'-n-pentylphenyl ester m.p. −5° C., K. 62° C.

EXAMPLE 14

49.2% 4-cyano-4'-n-pentylbiphenyl
26.4% 4-cyano-4'-n-heptylbiphenyl
15.5% 4-cyano-4'-n-octyloxybiphenyl
8.9% 4-(4-n-pentylphenyl)-benzoic acid 4'-n-pentylphenyl ester m.p. −5° C., K. 62° C.

EXAMPLE 15

50.8% 4-cyano-4'-n-pentylbiphenyl
27.3% 4-cyano-4'-n-heptylbiphenyl
16.0% 4-cyano-4'-n-octyloxybiphenyl
5.9% 4-(4-n-pentylphenyl)-benzoic acid 4'-methoxyphenyl ester m.p. < −10° C., K. 57° C.

EXAMPLE 16

49.7% 4-cyano-4'-n-pentylbiphenyl
26.7% 4-cyano-4'-n-heptylbiphenyl
15.6% 4-cyano-4'-n-octyloxybiphenyl
4.1% 4-(4-n-pentylphenyl)-benzoic acid 4'-methoxyphenyl ester
3.9% 4-(4-n-pentylphenyl)-benzoic acid 4'-pentylphenyl ester m.p. 0° C., K. 60°C.

EXAMPLE 17

36.4% 4-cyano-4'-n-pentylbiphenyl
20.6% 4-cyano-4'-n-heptylbiphenyl
11.2% 4-cyano-4'-n-pentyloxybiphenyl
11.2% 4-cyano-4'-n-heptyloxybiphenyl
13.1% 4-cyano-4'-n-octyloxybiphenyl
7.5% 4-(4-n-pentylphenyl)-benzoic acid 4'-n-pentylphenyl ester m.p. −10° C., K. 61° C.

EXAMPLE 18

40% anisic acid 4-n-pentylphenyl ester
22% 4-n-hexyloxybenzoic acid 4' pentylphenyl ester
31% 4-n-pentylbenzoic acid 4-n-pentyloxyphenyl ester
7% 4-(4-n-pentylphenyl)-benzoic acid 4'-pentylphenyl ester
m.p. 0° C., K. 60° C.

EXAMPLE 19

40% anisic acid 4-n-pentylphenyl ester
22% 4-n-hexyloxybenzoic acid 4'-n-pentylphenyl ester
31% 4-n-pentylbenzoic acid 4'-n-pentyloxyphenyl ester
7% 4-(4-n-pentylphenyl)-benzoic acid 4'-propylphenyl ester m.p. 2° C., K 60° C.

EXAMPLE 20

40% anisic acid 4-n-pentylphenyl ester
22% 4-n-hexyloxybenzoic acid 4'-n-pentylphenyl ester
31% 4-n-pentylbenzoic acid 4'-n-pentyloxyphenyl ester
7% 4-(4-n-pentylphenyl)-benzoic acid 4'-methoxyphenyl ester m.p. < −10° C., K. 61°C.

EXAMPLE 21

39% anisic acid 4-n-pentylphenyl ester
39% 4-n-hexyloxy benzoic acid 4'-n-pentylphenyl ester
22% 4-[4-(2-methyl butyl)-phenyl-]-benzoic acid 4'-n-pentylphenyl ester m.p. 7° C., K. 69° C.

The preceding examples can be repeated with similar success by substituting the generically or specifically described reactants and/or operating conditions of this invention for those used in the proceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A biphenyl ester of the formula

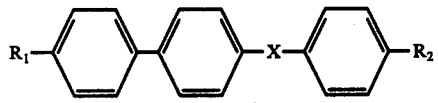

wherein X is —CO—O— or —O—CO— and $R_1$ and $R_2$ each are alkyl or alkoxy of 1-8 carbon atoms.

2. A biphenyl ester of claim 1 wherein X is —CO—O—.

3. A biphenyl ester of claim 1 wherein X is —O—CO—.

4. A biphenyl ester of claim 1 wherein at least one of $R_1$ and $R_2$ is alkyl.

5. A biphenyl ester of claim 4 wherein both $R_1$ and $R_2$ are alkyl.

6. A biphenyl ester of claim 5 wherein one of $R_1$ and $R_2$ is straight-chain alkyl of 1-7 carbon atoms and the other is alkyl of 3-8 atoms.

7. A biphenyl ester of claim 1 wherein one of $R_1$ and $R_2$ is alkyl and the other is straight-chain alkoxy.

8. A biphenyl ester of claim 7 wherein alkyl is straight-chain alkyl of 3-8 carbon atoms.

9. A biphenyl ester of claim 7 wherein the straight-chain alkoxy is of 1-6 carbon atoms.

10. A compound of claim 1, 4-(4-n-pentylphenyl)-benzoic acid 4′-n-pentylphenyl ester.

11. A compound of claim 1, 4-(4-n-pentylphenyl)-benzoic acid 4′-n-butylphenyl ester.

12. A compound of claim 1, 4-(4-n-pentylphenyl)-benzoic acid 4′-methoxyphenyl ester.

13. A compound of claim 1, 4-n-hexyloxybenzoic acid 4′-(4-pentylphenyl)-phenyl ester.

14. A compound of claim 1, 4-(4-n-pentylphenyl)-benzoic acid 4′-n-propylphenyl ester.

* * * * *